US010213098B2

(12) United States Patent
    Goldfain

(10) Patent No.: US 10,213,098 B2
(45) Date of Patent: Feb. 26, 2019

(54) LASER CONFIGURED OTOSCOPE

(71) Applicant: Welch Allyn, Inc., Skaneateles Falls, NY (US)

(72) Inventor: Ervin Goldfain, Syracuse, NY (US)

(73) Assignee: Welch Allyn, Inc., Skaneateles Falls, NY (US)

(*) Notice: Subject to any disclaimer, the term of this patent is extended or adjusted under 35 U.S.C. 154(b) by 727 days.

(21) Appl. No.: 14/532,524

(22) Filed: Nov. 4, 2014

(65) Prior Publication Data

US 2015/0133732 A1    May 14, 2015

Related U.S. Application Data

(60) Provisional application No. 61/901,756, filed on Nov. 8, 2013.

(51) Int. Cl.
| | |
|---|---|
| *A61B 1/227* | (2006.01) |
| *A61B 1/00* | (2006.01) |
| *A61B 1/06* | (2006.01) |
| *G02B 27/12* | (2006.01) |

(52) U.S. Cl.
    CPC .......... *A61B 1/227* (2013.01); *A61B 1/00096* (2013.01); *A61B 1/0684* (2013.01); *G02B 27/126* (2013.01)

(58) Field of Classification Search
    CPC .................................................. A61B 1/227
    USPC ................................ 600/199, 200, 245–249
    See application file for complete search history.

(56) References Cited

U.S. PATENT DOCUMENTS

| | | | | |
|---|---|---|---|---|
| 3,978,850 | A | * 9/1976 | Moore | .................... A61B 1/227 600/200 |
| 4,006,738 | A | * 2/1977 | Moore | .................... A61B 1/07 385/117 |
| 4,622,967 | A | 11/1986 | Schachar | |
| 4,913,132 | A | 4/1990 | Gabriel | |
| 5,714,832 | A | * 2/1998 | Shirrod | .................. A61B 1/227 310/328 |

(Continued)

FOREIGN PATENT DOCUMENTS

| | | |
|---|---|---|
| DE | 44 28 773 A1 | 2/1996 |
| WO | WO 2009/157825 A1 | 12/2009 |
| WO | WO 2012/061697 A1 | 5/2012 |

OTHER PUBLICATIONS

Laser otoscope Source: http://mds.clevelandelinic.org/Services/Engineering/Portfolio.aspx?n=505 Date Accessed: Jun. 7, 2013.

(Continued)

*Primary Examiner* — Matthew J Lawson
*Assistant Examiner* — Amy R Sipp
(74) *Attorney, Agent, or Firm* — Barclay Damon, LLP

(57) ABSTRACT

An otoscopic instrument includes an instrument housing having a distal end and an opposing proximal end, each end defining a viewing axis of the instrument. A laser light source is disposed in relation to the viewing axis. At least one optical element is configured to direct emitted light from the laser light source toward a target of interest through the distal end of the instrument housing and in which reflected laser light is directed toward the proximal end along the viewing axis. The laser light source can be contained within a releasably attachable laser module to selectively permit separate white light and laser viewing modes of the instrument.

14 Claims, 5 Drawing Sheets

(56) References Cited

U.S. PATENT DOCUMENTS

| | | | |
|---|---|---|---|
| 5,951,543 A | 9/1999 | Brauer | |
| 6,106,457 A * | 8/2000 | Perkins | A61B 1/00041 396/312 |
| 6,475,138 B1 | 11/2002 | Schechter et al. | |
| 6,704,053 B1 * | 3/2004 | Niikawa | H04N 5/2254 348/335 |
| 7,331,954 B2 | 2/2008 | Temelkuran et al. | |
| 8,197,403 B2 | 6/2012 | Strom et al. | |
| 2003/0036680 A1 | 2/2003 | Black | |
| 2003/0100819 A1 * | 5/2003 | Newman | A61B 1/00052 600/300 |
| 2003/0171655 A1 | 9/2003 | Newman et al. | |
| 2005/0171399 A1 * | 8/2005 | Rich | A61B 1/00048 600/112 |
| 2006/0282009 A1 | 12/2006 | Oberg et al. | |
| 2009/0185191 A1 * | 7/2009 | Boppart | A61B 5/0066 356/479 |
| 2011/0152621 A1 | 6/2011 | Mendes et al. | |
| 2013/0036680 A1 | 2/2013 | Noble | |
| 2013/0123641 A1 * | 5/2013 | Goldfain | A61B 5/0066 600/476 |
| 2013/0128223 A1 | 5/2013 | Wood et al. | |

OTHER PUBLICATIONS

Flores-Moreno et al., "Holographic otoscope for nanodisplacement measurements of surfaces under dynamic excitation", Center for Holographic Studies and Laser micro-mechaTronics, WPI, Worcester, MA 01609, USA. mflores@wpi.edu Scanning. Sep.-Oct. 2011;33(5):342-52. doi: 10.1002/sca.20283. Epub Sep. 6, 2011.

Huli, "Development of an optoelectronic holographic otoscope system for characterization of sound-induced displacements in tympanic membranes" Source: http://www.wpi.edu/Pubs/ETD/Available/etd-011309-095519/unrestricted/nhulli.pdf. Date Accessed: Jun. 7, 2013.

Sedlmaier et al., "The CO2 Laser Otoscope. A New Application Device for Paracentesis", Klinik mit Polikliniken, Klinikum Benjamin Franklin, Freie Universität Berlin. HNO. Oct. 1998; 46(10):870-5 (Abstract).

* cited by examiner

LASER CONFIGURED OTOSCOPE

CROSS REFERENCE TO RELATED APPLICATION

This application claims priority under relevant sections of 35 U.S.C. § 111 and 37 CFR § 1.53 to U.S. Application Ser. No. 61/901,756, entitled LASER CONFIGURED OTOSCOPE, filed Nov. 8, 2013, the entire contents of which are herein incorporated by reference.

TECHNICAL FIELD

This application generally relates to the field of diagnostic medicine and more specifically to an otoscopic instrument that is configured with a laser light source.

BACKGROUND

Otoscopes are very well known hand-held medical diagnostic instruments used for examining the ear of a patient. A typical otoscope 20, illustrated in FIG. 1, is defined by an instrument head 22 that is supported by a handle portion 24. The handle portion 24 has an interior that is sized to retain a set of batteries 26 as well as an integrated white light source 28, such as an incandescent bulb, the latter usually being disposed within an upper part of the handle portion 24. The output of the illumination source 28 is coupled to the polished proximal end of a set of optical fibers 32 that upwardly extend from the handle portion 24 and through a necked portion of the instrument 20. The optical fibers 32 are configured to encircle the distal end of an axisymmetric insertion portion 36, the latter being formed at the distal end of the instrument head 22. A hollow disposable speculum tip 40 is releasably attached to the exterior of the axisymmetric insertion portion 36, the speculum tip 40 also being defined by a tapered axisymmetric configuration and having respective proximal and distal tip openings 41, 42. A viewing window 50 is provided at the proximal end 25 of the instrument head 22. The viewing window 50 can include a magnifying optic 54.

In use, the speculum tip 40 (shown in phantom in this view) is releasably attached to the distal axisymmetric insertion portion 36 of the instrument head 24. The speculum tip 40 includes an internal feature (not shown) that engages a circumferential bayonet slot 39 provided on the exterior of the axisymmetric insertion portion 36 wherein the tip 40 is twisted rotationally in a locking direction to secure the speculum tip 40 in place. The shape of the speculum tip 40 permits insertion only to a predetermined depth within the outer ear of a patient (not shown). The contained illumination source 28 is typically activated by a user actuable switch 43 that is provided on the handle portion 24 after the speculum tip 40 has been attached to the otoscope 10 in which a ringlet of white light is provided at the distal opening 38 of the axisymmetric insertion portion 36 for illuminating the target. The amount of illumination for examination can optionally be adjusted using a rheostat (not shown). The outer ear, including the tympanic membrane (not shown), can then be examined for otitis media or other signs of infection that can be seen by the caregiver through the viewing window 50.

In other versions, specific optical systems can be provided within the instrument head, such as those found in otoscopes manufactured and sold by Welch Allyn, Inc. under the tradename of Macroview that permits viewing of the entire tympanic membrane all at once, as discussed in U.S. Pat. No. 8,197,403B1, herein incorporated by reference, whether visually or using an electronic imager.

Still other versions can incorporate other specific illumination systems to direct emitted light from a light source toward the target of interest using various means disposed within the instrument head. For example, some otoscopes may utilize a light pipe or waveguide while other systems may provide illumination of a ringlet of optical fibers or alternatively a circumferential array of small LEDs. Still other systems may provide direct illumination relative to the target of interest.

Recently, it has been discovered that utilization of a low power laser light source can provide enhancements to ear examinations and more specifically enable the detection of fluid behind the tympanic membrane; (i.e., effusion in the middle ear which can be deduced from a reflectance pattern obtained from an emitted laser light that passes through, but does not puncture the tympanic membrane). Providing this additional capability would be extremely advantageous for a caregiver to enable a more comprehensive examination of a patient. For example, it is difficult to reliably discern whether an ear infection is viral or bacterial in nature. This distinction is important in that antibiotics are usually an effective treatment against viral infections, but are wholly ineffective against bacterial infections. Because of the above noted difficulty to discern an identified ear infection, antibiotics are often prescribed as a matter of routine. In the course of this latter discovery, a need has therefore developed in the field to be able to readily incorporate a low power laser light source for use in an otoscopic instrument. There is an equally compelling need to be able to be incorporate or retrofit such a feature in existing otoscopic instruments, if possible.

BRIEF DESCRIPTION

Therefore and according to one aspect, there is provided an otoscope comprising an instrument housing having a distal end and a opposite proximal end, the ends of the housing being aligned along a viewing axis of the instrument. A laser light source disposed within the housing or attached thereto is configured to direct an emitted beam towards a target of interest for projection thereon and in which reflected laser light is directed toward the proximal end of the instrument housing along the viewing axis.

In one version, the laser light source is disposed within a laser module that can be releasably attached to the instrument housing, such as to the proximal end thereof. The laser module comprises a module housing retaining the laser light source and at least one optical element that is configured to guide light emitted from the laser source along an illumination axis to a target of interest (e.g., the outer and middle ear), wherein the laser module is further configured to receive reflected light from the target of interest for viewing by a caregiver along the viewing axis.

In at least one version, the laser module further comprises viewing optics, such as a magnifying lens that is aligned with a viewing axis of the instrument. Additional optical elements, such as polarizers and filters, can also be supported and aligned by the laser module housing for enhanced viewing.

The at least one optical element can include a mirror, a beamsplitter or other suitable optic having a surface that is configured to guide emitted laser light to the distal end of the instrument and to the target of interest. According to at least one version, the optical element can be configured along the viewing axis of the instrument whether integrally or upon attachment of a laser module retaining the optical element.

The laser light source can be used in conjunction with a white light source of an existing otoscopic instrument to enable comprehensive ear examinations. The simultaneous use of both laser light and white light sources, however, may compromise overall performance. Therefore and according to one version, the instrument may be configured such to disable operation of the laser light source while the white light source is operating. For example and in one embodiment, the output of the white light source can be detected using at least one light detection element and wherein energization of the laser source is disabled until a signal or a lack of signal is provided by the light detection element that is indicative that the white light source has either been turned off or is operating at a sufficiently low output level. By disposing the at least one optical element along the viewing axis, a portion of reflected light can be advantageously diverted to the at least one light detection element. Depending on the design/configuration of the optical element and according to at least one version, the laser light source and the light detection element can be mounted to a common circuit board, the latter having processing logic for controlling the operating of the laser light source depending on light output detected.

According to another aspect, there is provided a laser module configured for use with an otoscopic instrument. The laser module comprises a module housing that retains a laser source. The module can include at least one attachment feature that permits releasable securement to the instrument housing. In at least one version and when the laser module is attached to the instrument, the retained laser source is arranged off-axis in relation to a viewing axis of the otoscope. The laser module can include at least one optical element, such as a beam splitter or a prism, that directs the emitted light to the target of interest.

According to yet another aspect, there is provided a method for enabling a laser for use in an otoscopic instrument, the method comprising the steps of providing a laser source, and configuring at least one optical element to direct an emitted laser beam along the illumination axis and towards a target of interest through the distal end of the otoscope along an illumination axis.

In one version, a laser module is configured for releasable attachment to an otoscope housing, the module being configured for retaining the laser light source, the optical element and viewing optics.

The laser source can be used in an otoscope having a conventional white light source. In one version, at least one light detection element is provided to indicate whether the white light source is operating and disabling the laser light source based upon the detection of white light.

One advantage provided by the herein described otoscopic instrument that is properly equipped with a laser light source is increased functionality that enables more comprehensive ear examinations of a patient.

Another advantage realized is that the presence of fluid in the middle ear can be more readily detected to facilitate the distinction between bacterial and viral infections involving the patient, thereby improving diagnosis and providing avoidance of costly and ineffective antibiotic prescriptions that can later compromise resistance to disease.

Yet another advantage from the present system is that already existing otoscopic instruments can immediately incorporate a laser assembly as described herein without significant modification or retrofitting being required.

This incorporation can be done relatively inexpensively wherein the resulting instrument is not increased in size to a degree that makes the enhanced examination more difficult or untenable for either the patient or the caregiver.

Yet another advantage provided is that the instrument can be easily configured to perform reliably in either a white light or a laser light operational mode.

Yet another advantage is the ability of the laser source to be either intensity modulated or to generate a light pattern on the tympanic membrane in order to facilitate distinction between a healthy ear and an infected ear or between bacterial or viral fluid.

These and other features and advantages will be readily apparent from the following Detailed Description, which should be read in conjunction with the accompanying drawings.

DETAILED DESCRIPTION

The following description relates to exemplary embodiments of an otoscopic instrument ("otoscope"). More specifically, these embodiments relate to the incorporation of a releasably attachable laser module to an existing otoscopic instrument design for enabling enhanced ear examinations of a patient. It will be understood, however, that the described module could alternatively be provided integrally as a feature of an otoscopic instrument. In addition and throughout the course of discussion, several terms are used in order to provide an adequate frame of reference with regard to the accompanying drawings. However, these terms, which may include "distal", "proximal", "upper", "lower", "above", "below" and the like are not intended to be limiting of the scope of the inventive concepts described herein, except where specifically indicated.

Figure 1:
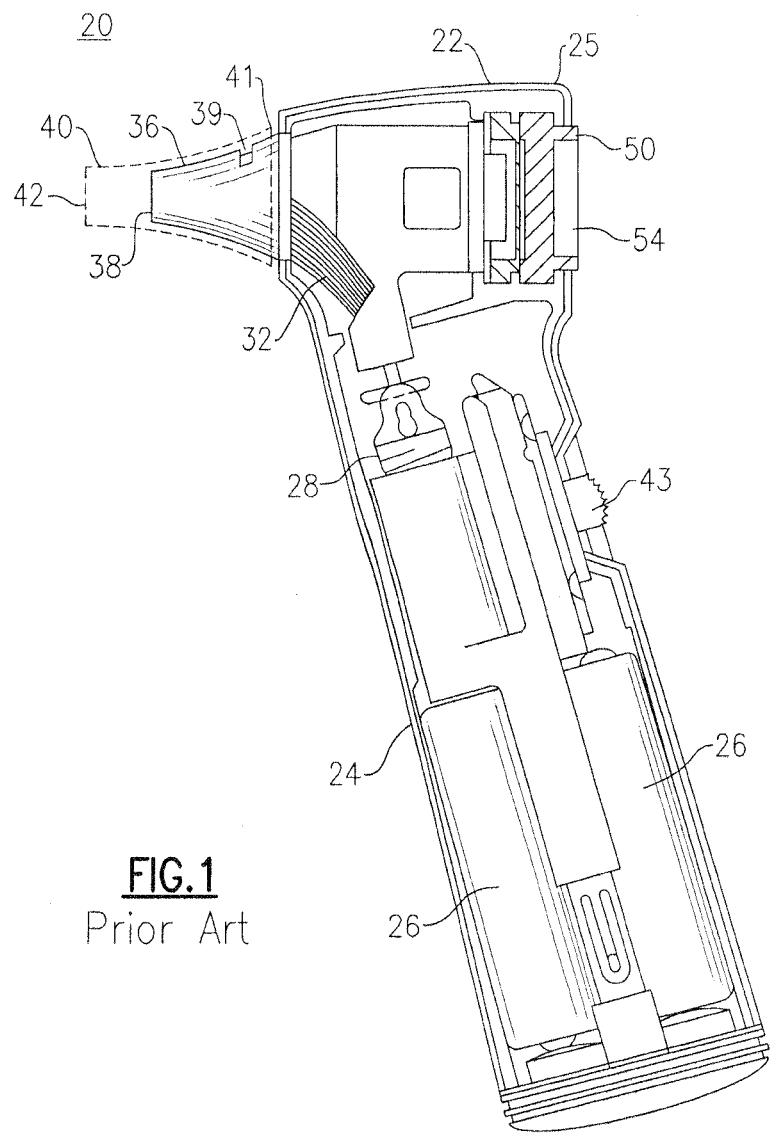
FIG. 1 is a side elevational view, taken partially in section, of a prior art otoscopic instrument.
Figure 2:
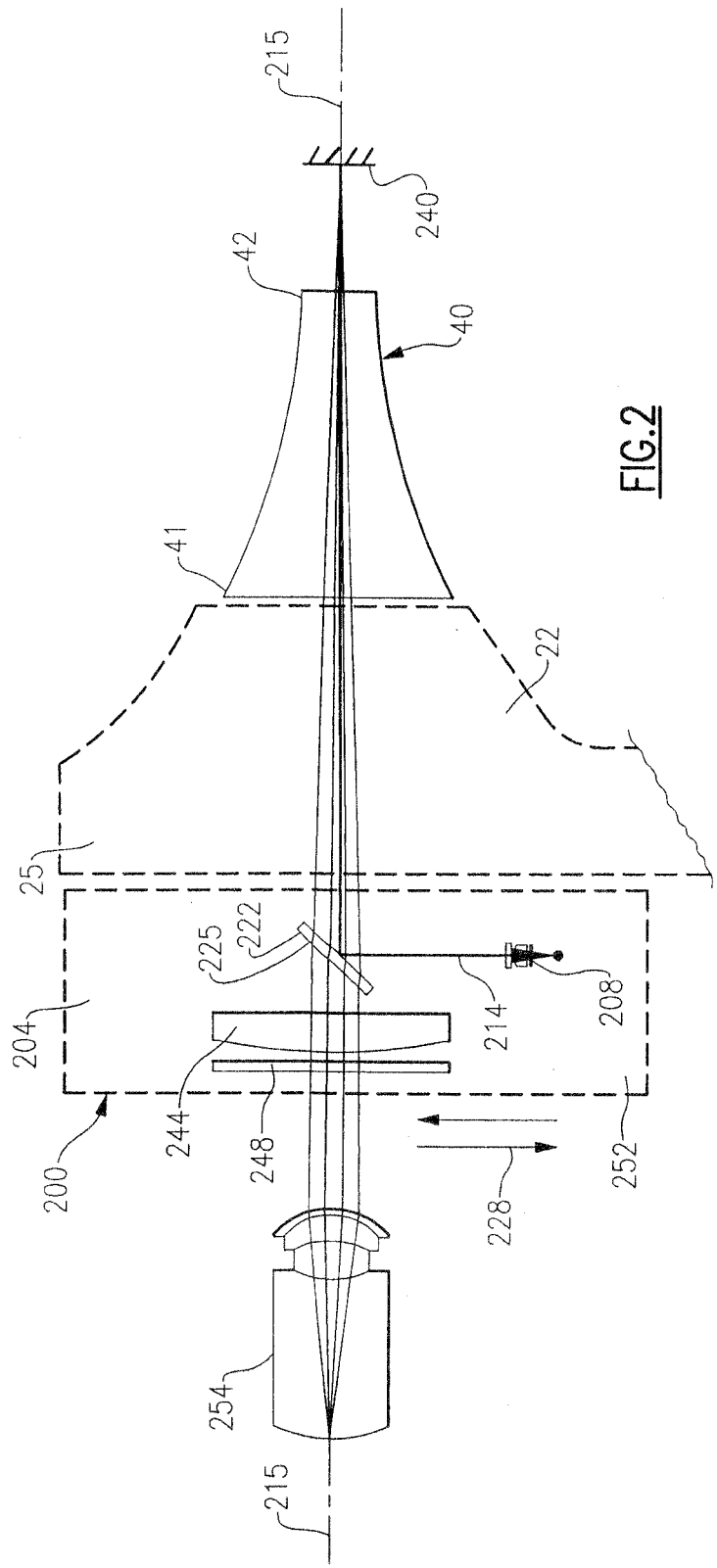
FIG. 2 is a side schematic view of an otoscope equipped with a laser module in accordance with an exemplary embodiment.
Figure 3:
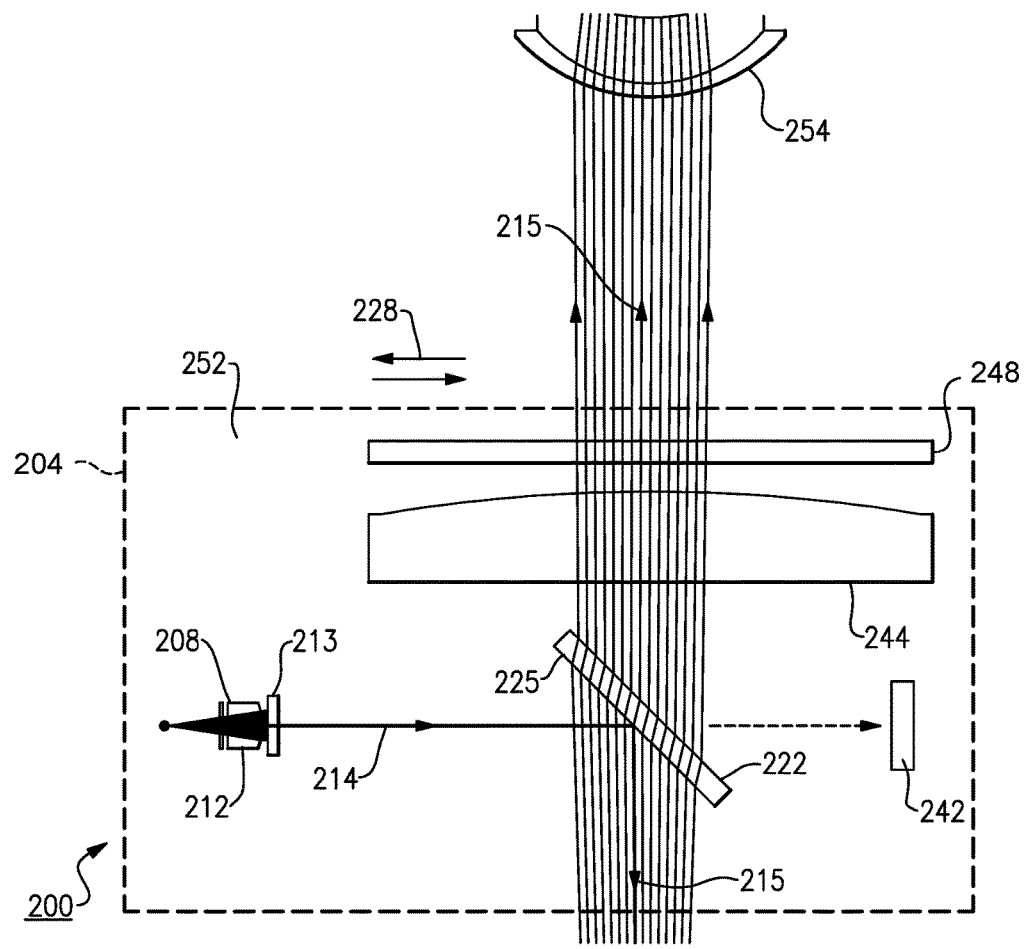
FIG. 3 is an enlarged view of the laser module of FIG. 2.

Referring to FIG. 2, there is shown a side schematic view of an otoscope that is configured with a laser light source in accordance with a first exemplary embodiment. For purposes of this specific discussion, the otoscope herein referred to is similar to that previously depicted in FIG. 1. In this version, a laser module 200 is configured for releasable attachment to the proximal end 25 of the instrument head 22 in lieu of the viewing window 50, FIG. 1, which has been removed. Referring to FIGS. 2 and 3, the laser module 200 according to this embodiment is defined by a module housing 204 that retains a laser light source, such as, for example, a laser diode 208 configured to emit light of a predetermined wavelength to produce a specific color such as green (532 nm) or red (635 nm). Preferably, the laser light source is a low power laser light source with a power rating of no more than about 10 mW. According to this embodiment, the laser diode 208 is mounted to a printed circuit board (not shown) by known means. A collimating lens 212 is aligned along an illumination axis 214 relative to the laser diode 208, as well as at least one linear polarizer 213. According to this embodiment, an aperture stop 211 is disposed between the collimating lens 212 and the polarizer 213 having an appropriate spacing to prevent the passage of stray light and to reduce incidence of glare. Each of the foregoing elements are securely fixed within the module housing 204 such that when assembled to the proximal end 25 of the otoscope 10, FIG. 1, the laser light source 208 is disposed in a fixed position that is angled relative to the viewing axis 215 of the instrument 200.

An optical element further maintained by the laser module 200, such as a beam splitter 222, is aligned along the illumination axis 214, as well as the viewing axis 215 of the instrument according to this exemplary embodiment. The beam splitter 222 includes an angled receiving surface 225 that is configured to direct a portion of the emitted laser light 210 along the viewing axis 215 of the instrument and towards the distal end thereof.

In this version, arrows 228 are shown indicating attachment and detachment directions of the laser module 200 with respect to the instrument head 22. The laser module 200 can include a dedicated power source (not shown) or can be alternatively configured for connection with the existing power supply (batteries 26, FIG. 1) of the instrument. In terms of attachment, each of the proximal end of the instrument head 22 and the module housing 204 can include mechanical attachment features, such as a dovetail connection, a bayonet connection, a threaded connection with a pre-adjusted setting being provided for correct angular orientation of the retained components, a snap-fitting mount or other suitable arrangement. To that end, it should be readily understood that any mechanical attachment features can be employed that properly align the optical and illumination components of the module to the instrument and secure them reliably can be employed for purposes described herein. It will be also readily understood that while a separable modular housing 204 is herein described, an otoscopic instrument could alternatively and integrally include a laser light source and optical elements, as described herein, in lieu of a releasable assembly.

When the module housing 204 is attached to the proximal end 25, FIG. 1, of the instrument and according to this specific embodiment, the emitted light beam from the retained laser diode 208 is collimated by the collimating lens 212, directed through the aperture stop and polarizer 213 and then further directed along the illumination axis 214 to the angled receiving surface 225 of the beam splitter 224. The latter angled surface 225 is configured to redirect the emitted light along the viewing axis 215 through the insertion portion 36, FIG. 1, and the distal end 42 of the speculum tip 40, the light being directed upon the tympanic membrane, shown schematically as 240 in FIG. 2. A portion of the light passing through the angled surface 225 of the beam splitter 222 is captured by a light trap 242, shown only in FIG. 3, configured within the module housing 204 and aligned with the illumination axis 214 to prevent back reflection and glare. The light trap 242 is attached to an interior wall or other portion of the module housing 204 and is defined by a light absorbing material, such as strongly absorbing glass, black paint or a pair of crossed linear polarizers.

The light reflected from the angled receiving surface 225 is directed through the distal end of the instrument and the distal tip opening 42 of an attached speculum tip 40 that is positioned within the ear along the viewing axis 215 of the instrument. This light is caused to pass through the tympanic membrane 240 wherein the reflected green laser light that can detect the presence of fluid behind the tympanic membrane 240 (effusion in the middle ear) is directed along the viewing axis 215 through the beam splitter 222 and an aligned magnifier lens 244 and polarizer 248, each disposed in a proximal end of the laser module housing 204 to permit viewing by a caregiver, whose eye is shown functionally in this view as 254. Alternatively, an imaging device (not shown), such as a smartphone, can be positioned and aligned to receive the resulting image.

As previously noted, it has been determined that the ability to adequately perceive images produced by the low power laser light source can be significantly compromised by the concurrent presence of incandescent (white) light from the light source 28, FIG. 1, of an existing otoscope 10, FIG. 1. If the laser module is configured for operation with an existing otoscope having a white light source, then the instrument should operate in separate examination or viewing modes; that is, a white light examination mode and a laser light examination mode.

Figure 4:
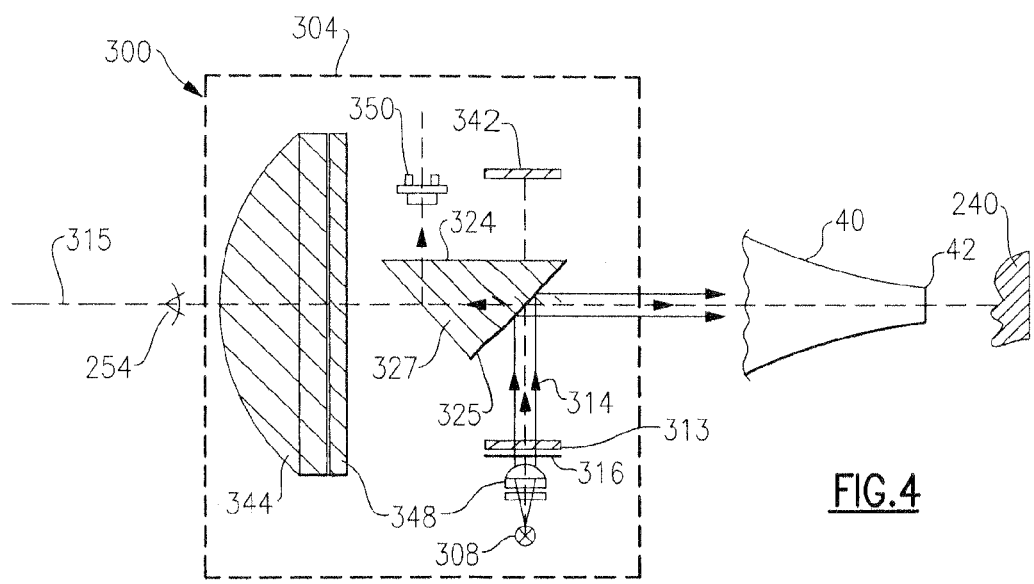
FIG. 4 is a side elevational view, taken in section, of a laser module made in accordance with another exemplary embodiment.

An alternative embodiment of a laser module is therefore shown in FIG. 4. As in the preceding, this module 300 is defined by a light-tight module housing 304 (shown schematically in this view) that is configured for attachment to the proximal end of an existing otoscope, such as the otoscope 10, FIG. 1. The module housing 304 fixedly retains a laser light source (such as a laser diode 308) configured to emit light of a predetermined wavelength to produce a specific color such as green or red. According to this embodiment, the laser diode 308 is mounted to a printed circuit board (not shown) by known means and is configured to emit light having a wavelength of 532 nanometers, thereby producing green colored light. A collimating lens 312 is disposed in alignment with the laser diode 308 along the illumination axis 314 along with an aperture stop 316 and at least one polarizer 313 or other glare reducing feature. According to this version and in lieu of a beam splitter as an optical element configured to direct illumination to the tympanic membrane 240, a prismatic member 324 is disposed along the illumination axis 314 to receive the collimated light beam emitted by the contained laser diode 308. The prismatic member 324 is configured to be positioned along the viewing axis 315 of the instrument when the module 300 is attached to the proximal end of the instrument head 22, FIG. 1. The laser diode 308 can be disposed upon a circuit board (not shown) and powered either by a separately contained power supply or by the power supply (i.e., batteries 26, FIG. 1) of the instrument.

The prismatic member 324 according to this embodiment is further defined by a proximal light receiving surface 327. A light detection element 350, such as a photo cell, is aligned with the proximal light receiving surface 327, the light detection element 350 being mounted to a printed circuit board (not shown) having suitable processing logic.

In use, the instrument can be used in a first white light examination mode in which the contained incandescent lamp 28, FIG. 1, can be used to examine the ear canal. Incandescent light is emitted from the optical fibers 32, FIG. 1, and directed along the viewing axis 315 of the instrument through the speculum tip 40 and is reflected from the tympanic membrane 240 and the interior of the ear canal. A portion of this reflected light can be diverted toward the light detecting element 350 when the light impinges upon the proximal angled surface 327 of the prismatic member 324. If the light detecting element 350 emits a signal indicative of the presence of white light along the viewing axis 315, then the retained laser source 308 is disabled from operation. Alternatively, the instrument can be configured to manually deactivate the white light source (incandescent lamp 28, FIG. 1) when a button is depressed, for example, on the instrument handle or the laser module housing 304 when examination using the low power laser light source 308 is opted for by a caregiver.

In the lack of presence of white light or a predetermined threshold level, the laser diode 308 can be activated for engaging the laser examination mode of the herein described instrument. In this latter examination mode, the emitted laser light beam is caused to pass through the collimating lens 312 and the aperture stop 316, the light being further directed through the at least one polarizer 313 along the illumination axis 314 to the distal angled surface 325 of the prismatic member 324. The latter angled surface 325 redirects the emitted and collimated laser light toward the distal end of the instrument head 22, FIG. 1, and through the distal opening 42 of an attached speculum tip 40 (shown partially in this view). Due to the transmissive nature of the prismatic member 324, the light sink or trap 342 disposed in relation to an interior wall of the module housing 308 is configured to prevent or at least minimize the incidence of glare as a result of reflected light in addition to the polarized elements and the aperture stop 316. The light trap 342 is defined by a suitable light absorbing material, such as strongly absorbing glass, black paint or a pair of crossed linear polarizers.

The incident green laser light, having a wavelength of approximately 532 nanometers, permits the detection of fluid behind the tympanic membrane 240 (within the middle ear) due to a diffuse reflection pattern, whereas a concentrated reflection pattern is indicative of no such fluid. Reflected light is then directed along the viewing axis 315 of the instrument and through the prismatic member 324. The reflected light passes through the distal angled surface 325 and the proximal angled surface 327 and is directed along the viewing axis 315 through a suitably aligned polarizer 348 and a magnifying lens 344 for viewing by the eye 254 of the caregiver or a suitable imaging device (not shown).

Figure 5:
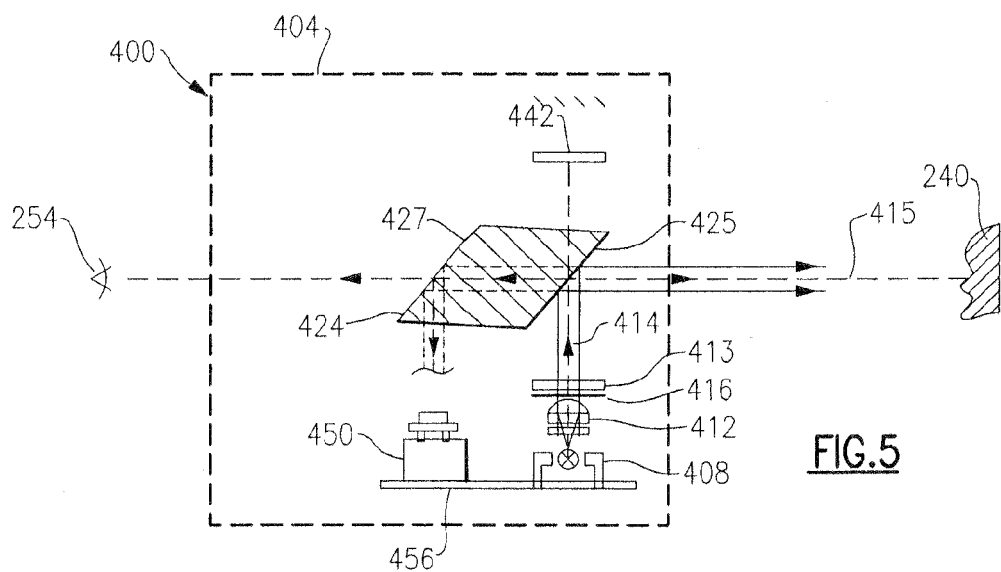
FIG. 5 is a side elevational view, of a laser module in accordance with another exemplary embodiment.

A laser module according to another exemplary embodiment is depicted in FIG. 5 for use with an existing otoscope 10, FIG. 1. According to this version, the laser module 400 is defined by a light-tight housing 404 (schematically shown in this view) that retains a laser light source, such as a laser diode 408, a collimating lens 412, an aperture stop 416 and at least one polarizer 413, each of these elements can be similar to those discussed in previously described embodiments and aligned along an illumination axis 414. The module housing 404 can be configured for releasable attachment to the proximal end 25, FIG. 1, of an otoscopic instrument head 22, FIG. 1. An optical element 424 is provided having parallel distal and proximal angled optical surfaces, 425, 427, in which the optical element 424 is defined by a suitably shaped and molded configuration. The distal angled surface 425 is aligned with the illumination axis 414 and configured to receive and direct the emitted laser light along the viewing axis 415 of the instrument and toward the distal end thereof. According to this embodiment, the laser light source 408 is mounted upon a circuit board 456 along with a light detection element 450, such as a photo cell, that is aligned with the proximal angled surface 427 and in which the printed circuit board 456 is further configured with suitable processing logic.

In use, the instrument is configured to operate in both a white light as well as laser light examination mode. In the white light examination mode, light from contained incandescent lamp 28, FIG. 1, is directed through the optical fiber bundle 32, FIG. 1, and directed to the ear canal of a patient through the distal tip opening 42, FIG. 1, of the speculum tip 40, FIG. 1. The light reflected from the ear canal is then directed as a diffuse reflectance pattern along the viewing axis 415 extending through the optical element 424 and toward the viewing window of the instrument. Operation of the contained laser light source 408 can be automatically conditioned upon the detection or lack of detection of a predetermined signal received from the light detection element 450 indicating that white light from the incandescent lamp 28 of the instrument is no longer present or is at a sufficiently low threshold level. The processing logic on the printed circuit board 456 according to at least one version is configured to automatically activate the laser light source 408 in the absence of reflected white light diverted from the proximal angled surface 427 of the optical element 424.

In the laser examination mode, the laser source 408 is enabled in which emitted light is directed along the viewing axis 415 and through the distal end (not shown) of the speculum tip (not shown). Laser light reflected from the target of interest (behind the tympanic membrane 240) is directed through the optical element 424 and toward the viewing window (not shown in this view) of the laser module 404 along the viewing axis 415 of the instrument. Other optical elements, such as polarizers, can also be provided to enhance viewing by the eye of the caregiver or alternatively using an attached imaging device, such as a smartphone.

Figure 6:
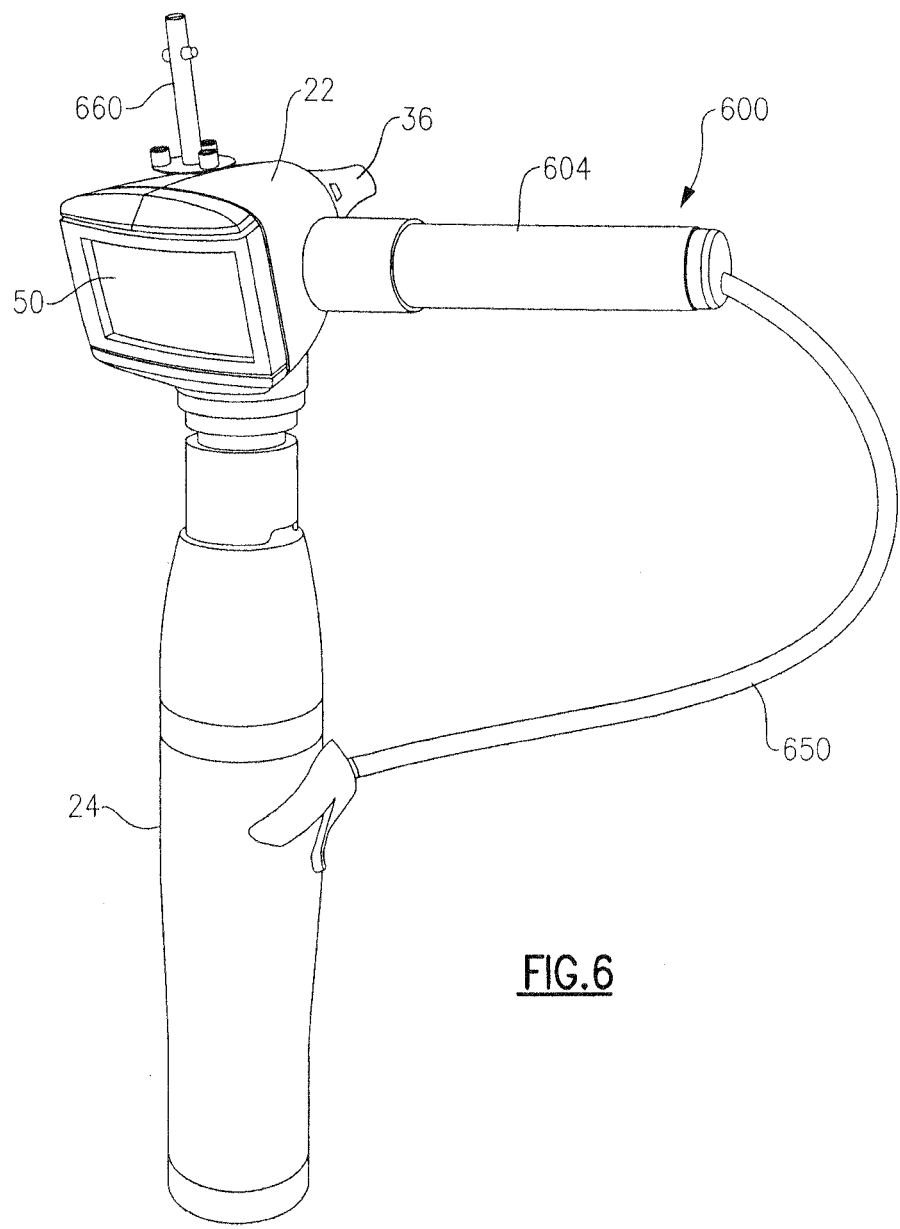
FIG. 6 is a perspective view of an otoscope configured with a laser module in accordance with another exemplary embodiment.

As previously discussed, the laser light module can be integrally provided as part of the housing or attached thereto. Referring to FIG. 6, another example of an attachable laser module 600 is provided in the form of a suitably shaped housing 604 that is caused to engage an existing otoscopic instrument 10. In this version, the housing 604 is substantially cylindrical in configuration and rather than being mounted to the proximal end of the instrument head 22, the laser module 600 in accordance with this embodiment is configured to be inserted through a side wall of the instrument head 22 such that the viewing window 50 of the instrument 10 can be retained. As in the preceding, the laser module housing 604 is configured to retain a low power laser source, such as shown in prior embodiments, as well as optics configured to direct an emitted laser beam to the target of interest (tympanic membrane). In this version and to further insure proper positioning of the laser module 600 and the retained components, a gimbal 660 or other positioning means can be added to control the position of the optical element (e.g., a beam splitter, prism or other) and to precisely aim the light emitted from the laser light source towards the target of interest either at the time of manufacture or in the field during use, if required. In this version, the laser module 600 can be powered by the contained batteries 26, FIG. 1, within the handle portion 24, in which an electrical tether 650 extends from the housing 604.

PARTS LIST FOR FIGS. 1-6

20 otoscope
22 instrument head
24 handle portion
25 proximal end
26 batteries
28 integrated light source
32 optical fibers
36 axisymmetric insertion portion
37 exterior surface
38 distal opening, insertion portion 39 bayonet slot
40 speculum tip
41 proximal tip opening
42 distal tip opening
43 actuable switch
45 proximal opening
50 viewing window
54 magnifying optic
200 laser module
204 module housing
208 laser light source
212 collimating lens
213 polarizer
214 illumination axis
215 viewing axis
222 beam splitter
225 angled surface
228 arrows
240 tympanic membrane
242 light trap
244 polarizer
248 magnifying lens
252 proximal end, housing
254 eye
300 laser module
304 module housing
308 laser diode
312 collimating lens
313 polarizer
314 illumination axis
315 viewing axis
316 aperture stop
324 prismatic member
325 distal angled surface
327 proximal angled surface
342 light trap
344 magnifying optic
348 polarizer
350 light detection element
400 laser light module
404 module housing
408 laser light source
412 collimating lens
413 polarizer
414 illumination axis
415 viewing axis
416 aperture stop
424 optical element
425 distal angled surface
427 proximal angled surface
442 light trap
450 light detection element
456 circuit board
600 laser light module
604 module housing
650 electrical tether
660 gimbal It will be readily apparent that other variations and modifications are possible to one or ordinary skill in the field that fall within the inventive aspects described in this application, including the attached claims.

The invention claimed is:

1. An otoscopic instrument comprising:
a handle having a retained white light source;
an instrument head attached to the top of the handle, the instrument head having a distal end and an opposing proximal end through which extends a viewing axis of the instrument, and in which a speculum tip is releasably attachable to the distal end;
a module housing having a distal end that is releasably attached to the proximal end of the instrument head, the module housing comprising:
an interior retaining a laser light source,
at least one optical element that directs emitted light from the laser light source toward a target of interest through the distal end of the instrument head, and a viewing optic disposed at a proximal end of the module housing; wherein reflected laser light from the target of interest is directed toward the proximal end of the instrument head along the viewing axis and further directed toward the viewing optic, which is aligned with the viewing axis, and in which the laser light source and the at least one optical element are aligned along an illumination axis that is transverse to the viewing axis of the instrument.

2. The instrument of claim 1, in which the module housing includes at least one feature to reduce incidence of glare.

3. The instrument of claim 1, including a feature for disabling the use of the laser source based on an operational condition of the white light source of the instrument.

4. The instrument of claim 1, wherein the at least one optical element is a beam splitter.

5. The instrument of claim 1, wherein the at least one optical element configured to direct emitted laser light is a prismatic member having at least one angled light transmissive surface directed along the viewing axis.

6. A laser module configured for use with an otoscopic instrument having an instrument head that includes a distal end, a proximal end, a viewing axis extending through the distal and proximal ends and in which a speculum tip is releasably attachable to the distal end, the laser module comprising:
a module housing having an interior;
a laser light source disposed within the interior of the module housing, said module housing being releasably attachable to the proximal end of the instrument head of the otoscopic instrument;
an optical element disposed within the interior of the module housing; and
a viewing optic disposed in a proximal end of the module housing, the optical element being aligned with the laser light source along an illumination axis and in which the optical element and the viewing optic are configured to align with the viewing axis of the otoscopic instrument when the module housing is attached to the instrument head with the illumination axis being transverse to the viewing axis.

7. The laser module as recited in claim 6, including at least one light detection element configured to detect the presence of white light along the viewing axis of the instrument and in which the laser light source is prevented from operating based on the detection of white light by the at least one light detection element.

8. The laser module as recited in claim 7, wherein the at least one light detection element and the laser light source are disposed commonly on a circuit board.

9. The laser module as recited in claim 6, wherein the optical element is a beamsplitter.

10. The laser module as recited in claim 6, wherein the optical element is a prism.

11. A method for configuring an otoscopic instrument for increased versatility, said method comprising:
providing an otoscopic instrument having an instrument head defined by a distal end, a proximal end, a viewing axis extending through the distal end and the proximal end, a speculum tip releasably attached to the distal end of the instrument head, providing a laser light source;

providing at least one optical element in alignment with the laser light source; and configuring the at least one optical element to direct an emitted laser beam from the laser light source towards a target of interest through a distal end of the otoscope; wherein the laser light source and the at least one optical element are disposed in a module housing along with a viewing optic disposed in a proximal end of the module housing, the method further comprising:

attaching the module housing to the proximal end of the instrument head such that the at least one optical element and the viewing optic are aligned with the viewing axis, and in which the laser light source and at least one optical element are aligned along an illumination axis that is transverse to the viewing axis.

12. The method of claim 11, including the step of providing at least one light detection element configured to detect the presence of white light and preventing use of the laser light source unless no white light or a sufficiently low level of white light is detected.

13. The method of claim 12, wherein the at least one detection element is a photocell.

14. The method of claim 12, in which the instrument includes a white light source and wherein the instrument is enabled to operate in a laser examination mode and a separate white light examination mode.

\* \* \* \* \*